| United States Patent [19] | [11] | 4,059,589 |
|---|---|---|
| Scherberich et al. | [45] | Nov. 22, 1977 |

[54] PROCESS FOR FORMYLATION

[75] Inventors: Paul Scherberich, Dietzenbach; Wolf-Dieter Pfeifer, Grossauheim, both of Germany

[73] Assignee: Deutsche Gold- und Silber-Schneideanstalt vormals Roessler, Frankfurt, Germany

[21] Appl. No.: 488,233

[22] Filed: July 12, 1974

[30] Foreign Application Priority Data

July 14, 1973 Germany .............................. 2335990

[51] Int. Cl.$^2$ ................. C07D 277/06; C07D 277/46; C07D 245/16

[52] U.S. Cl. .......................... 260/306.7 C; 260/268 C; 260/293.89; 260/306.8 R; 260/561 R; 260/562 R

[58] Field of Search .................... 260/306.7 C, 268 C, 260/293.89, 306.8 R, 561 R, 562 R

[56] References Cited

U.S. PATENT DOCUMENTS 2,450,784  10/1948  Duffin et al. .................. 260/306.7 C

OTHER PUBLICATIONS

Buehler et al., Survey of Organic Syntheses, Wiley-Interscience, N.Y., 1970, p. 898.
The Chemistry of Penicillins, Princeton Univ. Press (1949), p. 960.

*Primary Examiner*—R. Gallagher
*Attorney, Agent, or Firm*—Cushman, Darby & Cushman

[57] ABSTRACT

Organic basic nitrogen compounds are formylated in the presence of acetic anhydride by adding the nitrogen compound as a salt and carrying out the formylation with an alkali or ammonium formate in an organic solvent having limited miscibility with water.

18 Claims, No Drawings

PROCESS FOR FORMYLATION

The present invention is directed to a process for the formylation of organic basic nitrogen compounds in the presence of acetic anhydride.

It is known to formylate amines with formic acid in the presence of acetic anhydride (Houben-Weyl, Vol. 11/2 (1958) pages 27 to 30). Thiazolidines are formylated in the same manner. However, the thiazolidines are added as salts and an equivalent amount of sodium formate is added. (The Chemistry of Penicilline, Princeton University Press (1949) pages 921 to 972). A disadvantage of this process is that the formylation agent, e.g., the formic acid, is used in large excess.

There has now been found a process for the formylation of organic basic nitrogen containing compounds in the presence of acetic anhydride characterized in that the nitrogen containing compounds are added as the salts and the formylation is carried out with an alkali formate, e.g, sodium formate or patassium formate or ammonium formate in an organic solvent having limited solubility in water. By limited solubility in water is meant that the solvent does not have a solubility over 50 grams per 100 grams of water, preferably not over 10 grams per 100 grams of water. This process eliminates the addition of formic acid which in the known processes always was necessary in large excess as the formylation agent. Surprisingly it is not necessary when using the formates in place of formic acid as the formylation agent to add similarly large amounts in excess; it is on the contrary advantages to use only equivalent amounts of the formate to the basic nitrogen compound.

The process of the invention is generally useful with organic basic nitrogen containing compounds. It is also suitable for the formylation of compounds which are acid sensitive and therefore cannot be formylated or can only be formylated to a limited amount using formic acid.

As organic basic nitrogen compounds there are understood to be included compounds which contain one or more of the groups:

$$R_1 - NH_2 \qquad (I)$$

and/or

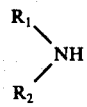   (II)

in which $R_1$ and $R_2$ are the same or different, i.e., the compounds are primary or secondary amines. There are especially to be considered compounds in which $R_1$ or $R_2$ are alkyl or alkenyl groups of up to 18 carbon atoms, e.g., alkyl of 1 to 18 carbon atoms or alkenyl of 3 to 18 carbon atoms, which can be straight chain or branched and in a given case are closed with the N-atom to form a ring. For example, there can be used methyl amine, dimethylamine, ethylamine, diethylamine, ethyl methyl amine, n-propyl amine, isopropylamine, diisopropylamine, sec. butyl amine, t-butyl amine, n-butyl amine, di-n-butylamine, di-sec. butylamine, cyclohexylamine, dicyclohexylamine, n-hexylamine, n-octylamine, n-dodceylamine, n-octadecylamine, 2-ethylhexylamine, allylanine, octen-4-yl-2-amine, oleyl amine, crotyl amine, diallyamine, piperidine, piperazine, pyrrolidine. $R_1$ and $R_2$ also can be alkyl or alkenyl of up to 18 carbon atoms substituted by halogen, e.g., chlorine, bromine, or fluorine, —OH, —SH, —OR, —SR or —COOR in which R is alkyl or alkenyl preferably with up to 6 carbon atoms, for example, 2-hydroxyethylamine, (ethonalamine), diethanolamine, isopropanolamine, propanolamine, dipropanolamine, 4-hydroxybutylamine, 6-hydroxyhexylamine, 2-chloroethylamine, 2-bromoethylamine, 2-fluoroethylamine, 3-chloropropylamine, di(3-chloropropyl)amine, 2-mercaptoethylamine, 4-mercaptobutylamine, 6-mercaptohexylamine, 2-methoxyethylamine, 2-ethoxyethylamine, 2-propoxyethylamine, 2-hexoxyethylamine, bis(2-ethoxyethyl)amine, 2-allyloxyethylamine, 3-ethoxypropylamine-1, 2-ethyl-2-aminoethylsulfide, methionine methyl ester, methionine ethyl ester, methionine propyl ester, methionine butyl ester, methionine isobutyl ester, methionine sec. butyl ester, methionine hexyl ester, penicillamine ethyl ester penicillamine methyl ester, penicillamine isopropyl ester, penicilllamine hexyl ester, valine isopropyl ester, alanine ethyl ester, glycine methyl ester, leucine propyl ester, isoleucine ethyl ester, penicillamine allyl ester, alanine crotyl ester. Furthermore, $R_1$ and $R_2$ can be aryl, aralkyl, alkylaryl or hetero aryl which in a given case can be substituted. e.g., benzylamine, aniline, N-methyl aniline, p-toluidine, o-toluidine, p-chloroaniline, 2-aminothiazole, 3-aminothiophene, 2-aminothiophene, α-phenylethylamine, diphenylamine.

The process of the invention is especially suitable for the formylation of thiazolidine-4-carboxylic acids of the formula:

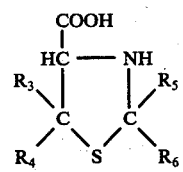   (III)

wherein $R_3$, $R_4$, $R_5$ and $R_6$ are the same or different. Preferably they are hydrogen or unbranched or branched, in a given case substituted, e.g., chlorosubstituted, alkyl, alkenyl, aryl, or alkylaryl groups, or $R_3$ and $R_4$ and/or $R_5$ and $R_6$ can be branched or unbranched in a given case substituted alkyl or alkenyl groups closed to a ring with the adjacent carbon atom. The alkyl or alkenyl groups preferably contain up to 6 carbon atoms but can contain up to 8 or more carbon atoms. The alkyl radicals in the alkylaryl groups preferably contain up to 3 carbon atoms. The alkyl or alkenyl group which are closed to a ring preferably contain 5 to 12 carbon atoms in the ring. The formylation of thiazolidine-4-carboxylic acids for example is required in the process of recovery of optically active penicillamines as an intermediate step in German Offenlegungschrift 2,138,122 and corresponding Asinger et al United States application 276,530 filed July 31, 1972 and now abandoned. The entire disclosure of the Asinger et al United States application is hereby incorporated by reference.

Examples of suitable thiazolidine-4-carboxylic acids are:

2,2,5,5-tetramethylthiazolidine-4-carboxylic acid (isopropylidine D,L-penicillamine), D,L-2,2-diethyl-5,5-dimethyl-thiazolidine-4-carboxylic acid, D,L-2,2-dioctyl-5,5-dimethyl-thiazolidine-4-carboxylic acid, D,L-2,2-dibutyl-5,5-dimethyl-thiazolidine-4-carboxylic acid,
D,L-2,2-diphenyl-5,5-dimethyl-thiazolidine-4-carboxylic acid,
2-isopropyl-5,5-dimethylthiazolidine-4-carboxylic acid,
2,2-pentamethylene-5,5-dimethyl-thiazolidine-4-carboxylic acid,
2,2-tetramethylene-5,5-dimethyl-thiazolidine-4-carboxylic acid,
2,2-pentamethylene-5,5-pentamethylene-thiazolidine-4-carboxylic acid,
2,2-di-n-propyl-5,5-dimethyl-thiazolidine-4-carboxylic acid,
2,2-dimethyl-thiazolidine-4-carboxylic acid,
2,2-dimethyl-5,5-pentamethylene-thiazolidine-4-carboxylic acid, thiazolidine-4-carboxylic acid,
2,2-diallyl-5,5-dimethylthiazolidine-4-carboxylic acid,
2,2-divinyl-5,5-dimethyl-thiazolidine-4-carboxylic acid,
2,5,5-trimethyl-2-vinyl-thiazolidine-4-carboxylic acid,
2,2-di-p-propylphenyl-5,5-dimethyl-thiazolidine-4-carboxylic acid.

The organic basic nitrogen compounds are added as salts, preferably salts of mineral acids. There can be used for example, salts of sulfuric acid, phosphoric acid, nitric acid and preferably the hydrohalic acids, e.g., hydrobromic acid, hydroiodic acid and especially hydrochloric acid. Especially the thiazolidine-4-carboxylic acids are used as salts of hydrochloric acid.

Desirably the acid used to form the salt is at least as strong as phosphoric acid.

As formylation agents in the invention there are used alkali formate or ammonium formate, preferably sodium formate or potassium formate. It is generally especially advantageous to add the formate and the nitrogen compound in amounts equivalent to each other. This is especially true in the case of the formylation of the thiazolidine-4-carboxylic acids. The choice of other molar amounts is possible, especially the use of excess amounts of formate. However, in most cases it is suitable to employ not over an excess of 100%, especially not over 20% excess of formate.

The reaction takes place in the presence of acetic anhydride. For each equivalent of nitrogen compound there is generally added about 1 to 4 moles, preferably about 1.5 to 2.5 moles, especially about 2.0 moles of acetic anhydride. It is also possible to use more than 4 moles of acetic anhydride per mole of nitrogen compound.

According to the process of the invention the formylation is carried out in an organic solvent which is inert and as stated above has limited miscibility with water. For example, there can be used aliphatic hydrocarbons such as petroleum ether, hexane, octane, decane and kerosene, halogenated aliphatic hydrocarbons such as methylene chloride, chloroform, carbon tetrachloride, ethylene dichloride, dichloroethylene, 1,1,2-trichloroethane, tetrachloroethane, aromatic hydrocarbons such as benzene, toluene, xylene and aromatic naphtha, ethers (including cyclic ethers) such as diethyl ether, dipropyl ether, dibutyl ether. Mixtures of solvents are useful, too. In many cases the preferred solvent to use depends on the properties of the materials to be reacted. Generally, particularly in the case of formylation of thiazolidine-4-carboxylic acids the aromatic hydrocarbons are preferred. The amount of solvent to be used in a given case is also dependent upon the properties of the materials to be reacted. Preferentially there are added 1 to 3 liters of solvent per mole of amine but the amount of solvent can be varied widely, e.g., there can be used up to 10 liters of solvent per mole of amine, but there is no limit.

The reaction generally takes place at temperatures of about 0° to 100° C., especially at temperatures of about 20° to 60° C. In the case of formylation of thiazolidine-4-carboxylic acids, preferably the temperature is about 20° to 50° C.

Unless otherwise indicated, all parts and percentages are by weight.

EXAMPLE 1

A mixture of 13 grams (0.1 mole) of aniline hydrochloride, 7.5 grams (0.11 mole) of water free sodium formate and 150 ml of petroleum ether were treated dropwise with 22.5 grams (0.22 mole) of acetic anhydride. Thereby the temperature of the mixture rose from 20° to 40° C. The mixture was stirred for 2 hours at 40° C. then cooled to 20° C. and washed twice, each time with 30 ml of water. Finally the petroleum ether was distilled off and the residue recrystallized from petroleum ether. There were recovered 10.5 grams of formanilide corresponding to an 87% yield. The formanilide had a melting point of 46° to 47° C.

EXAMPLE 2

The procedure was the same as in Example 1 except that there were added 12 grams (0.1 mole) of piperidine hydrochloride as the basic nitrogen compound salt and there was used 100 ml of benzene as the solvent. The yield of N-formylpiperidine was 7.9 grams, corresponding to a 70% yield. The substance has a boiling point of 100° to 104° C. at 16 millibars.

EXAMPLE 3

There were employed 16 grams (0.10 mole) of piperazine hydrochloride in 150 ml of toluene, 15 grams (0.22 mole) of sodium formate and 45 grams (0.44 mole) of acetic anhydride. The mixture was held for 4 hours at 40° to 45° C., then cooled to 20° C. and washed twice, each time with 50 ml of water. There were recovered 12 grams of 1,4-diformyl piperazine, corresponding to a yield of 85%. The substance has a melting point of 125° to 127° C.

EXAMPLE 4

A mixture of 22.5 grams (0.10 mole) of 2,2,5,5-tetramethyl thiazolidine-4-carboxylic acid hydrochloride, 7.5 grams (0.11 mole) of sodium formate, 22.5 grams (0.22 mole) of acetic anhydride and 150 ml of toluene were held for 5 hours at 40° C. There were recovered 18.5 grams of 3-formyl-2,2,5,5-tetramethyl-thiazolidine-4-carboxylic acid, corresponding to a yield of 85%. The substance had a melting point of 139° to 141° C.

EXAMPLE 5

27.5 grams (0.2 mole) of 2-aminothiazole hydrochloride and 13.6 grams (0.2 mole) of sodium formate were suspended in 100 ml of benzene. There were added dropwise at 40° to 45° C. 41 grams (0.4 mole) of acetic anhydride. The mixture was held at 40° to 45° C. for 2 hours, then cooled to 20° C., washed twice, each time with 50 ml of water and subsequently evaporated to dryness under reduced pressure. There were recovered 21 grams of 2-formylaminothiazole, corresponding to a yield of 82%. The substance had a melting point of 142° to 143° C.

EXAMPLE 6

To a suspension of 81.5 grams (1 mole) of dimethylamine hydrochloride and 68 grams (1 mole) of sodium formate in 500 ml of benzene there were added dropwise 204 grams (2 moles) of acetic anhydride. The temperature of the mixture rose thereby from 20° to 40° C. the mixture was treated further as in Example 1. In the final fractional distillation at normal pressure there were obtained 62 grams of dimethyl formamide, corresponding to a yield of 85%. The dimethyl formamide had a boiling point of 154° to 155° C. at 1 bar.

EXAMPLE 7

To a suspension of 24 grams (0.1 mole) of 2-isopropyl-5,5-dimethyl-thiazolidine-4-carboxylic acid hydrochloride and 6.8 grams (0.1 mole) of anhydrous sodium formate in 100 ml of benzene there were added dropwise 20 grams (0.2 mole) of acetic anhydride. Thereby the temperature of the mixture rose from 20° to 40° C. The mixture was held for 2 hours at 40° C., then washed twice, each time with 50 ml of water and evaporated to dryness under reduced pressure. The residue was dissolved in ethyl acetate, the solution filtered and treated with petroleum ether (boiling point 60° to 80° C.) until turbidity. There precipitated 17 grams of 3-formyl-2-isopropyl-5,5-dimethyl-thiazolidine-4-carboxylic acid, corresponding to a 73% yield. The substance had a melting point of 106° to 108° C.

EXAMPLE 8

The process of Example 7 was followed, but there were employed 25.2 grams (0.1 mole) of 2-isopropyl-5,5-dimethylthiazolidine-4-carboxylic acid sulfate and 8.5 grams (0.1 mole) of potassium formate. The yield of 3-formyl-2-isopropyl-5,5-dimethyl-thiazolidine-4-carboxylic acid amounted to 16.5 grams, corresponding to 71%. the substance had a melting point of 105° to 107° C.

EXAMPLE 9

The procedure of Example 7 was followed but there were used 31 grams (0.1 mole) of 2-(4-chlorophenyl)-5,5-dimethyl-thiazolidine-4-carboxylic acid hydrochloride, 8.5 grams (0.1 mole) of potassium formate and 100 ml of toluene. The reaction time was 3 hours. There were recovered 18.5 grams of 3-formyl-2-(4-chlorophenyl)-5,5-dimethyl thiazolidine-4-carboxylic acid, corresponding to a yield of 62%. The substance had a melting point of 167° to 168° C.

EXAMPLE 10

The procedure of Example 7 was followed but there were used 32.5 grams (0.1 mole) of 2,2-pentamethylene-5,5-dimethyl thiazolidine-4-carboxylic acid dihydrogen phosphate and 20 grams (0.3 mole) of sodium formate in 150 ml of chloroform. The product was recrystallized from toluene. There were obtained 22 grams of 3-formyl-2,2-pentamethylene-5,5-dimethyl thiazolidine-4-carboxylic acid, corresponding to a yield of 85%. The substance had a melting point of 166° to 168° C.

EXAMPLE 11

There was prepared a mixture from 29.6 grams (0.1 mole) of 2,2-tetramethylene-5,5-dimethyl thiazolidine-4-carboxylic acid hydrobromide, 6.8 grams (0.1 mole) of sodium formate, 20 grams (0.2 mole) of acetic anhydride and 100 ml of methylene chloride. The mixture was heated at reflux for 3 hours and then evaporated to dryness. The residue was recrystallized from water. There were recovered 20 grams of 3-formyl-2,2-tetramethylene-5,5-dimethyl thiazolidine-4-carboxylic acid, corresponding to a yield of 82%. The substance had a melting point of 156° to 157° C.

EXAMPLE 12

The procedure of Example 7 was followed but there was used 28 grams (0.1 mole) of 2,2-di-n-propyl-5,5-dimethyl thiazolidine-4-carboxylic acid hydrochloride. The product was recrystallized from toluene. There were recovered 19 grams of 3-formyl-2,2-di-n-propyl-5,5-dimethyl thiazolidine-4-carboxylic acid, corresponding to a yield of 70%. The substance had a melting point of 161° to 162° C.

EXAMPLE 13

A mixture of 20 grams (0.1 mole) of 2,2-dimethyl thiazolidine-4-carboxylic acid hydrochloride and 6.8 grams (0.1 mole) of sodium formate in 150 ml of toluene were treated with 20 grams (0.2 mole) of acetic anhydride at 45° C. The mixture was for 4 hours held at 45° C. The product separating as a solid was filtered off and recrystallized from water. There were recovered 15 grams of 3-formyl-2,2-dimethyl-thiazolidine-4-carboxylic acid, corresponding to a yield of 79%. The substance had a melting point of 216° to 217° C.

EXAMPLE 14

The procedure of Example 7 was followed, but there were used 26.5 grams (0.1 mole) of 2,2-dimethyl-5,5-pentamethylene thiazolidine-4-carboxylic acid hydrochloride. The product was recrystallized from water. There were recovered 21 grams of 3-formyl-2,2-dimethyl-5,5-pentamethylene thiazolidine-4-carboxylic acid, corresponding to a yield of 82%. The substance had a melting point of 201° to 202° C.

What is claimed is:

1. In a process for the formylation of an organic basic nitrogen compound having at least a hydrogen atom attached to the basic nitrogen atom in the presence of acetic anhydride, the improvement comprising adding the nitrogen compound as a salt with an acid and carrying out the formylation without formic acid and with an alkali formate or ammonium formate in an inert organic solvent having limited solubility in water.

2. A process according to claim 1 wherein there are used about equivalent amounts of nitrogen compound and formate.

3. A process according to claim 1 wherein the solvent is an aliphatic hydrocarbon, an aromatic hydrocarbon, an aliphatic halohydrocarbon or an ether.

4. A process according to claim 1 wherein the organic basic nitrogen compound is free of substituents which react with the formate.

5. A process according to claim 4 wherein the organic nitrogen compound has the formula

$$R_1 - NH_2 \qquad (I)$$

, or

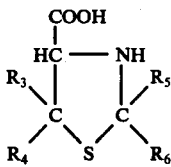

(III)

wherein $R_1$ and $R_2$ are alkyl, alkenyl, aryl, aralkyl, alkaryl, heterocyclic, alkyl or alkenyl substituted with halogen, —OH, —SH, —OR, —SR or —COOR where R is alkyl or alkenyl or $R_1$ and $R_2$ together are polymethylene and are joined with the basic nitrogen atom and up to 1 additional nitrogen atom to form a 5 to 6 membered ring, $R_3$, $R_4$, $R_5$ and $R_6$ are hydrogen, alkyl, alkenyl, aryl, alkaryl or at least one of the pairs $R_3$ and $R_4$ and $R_5$ and $R_6$ are polymethylene and joined together with the adjacent carbon atom of the thiazolidine ring to form a cycloaliphatic ring of 5 to 12 carbon atoms.

6. A process according to claim 5, wherein $R_1$ and $R_2$ are alkyl of up to 18 carbon atoms, alkenyl of up to 18 carbon atoms, phenyl, benzyl, tolyl, alkyl of up to 18 carbon atoms substituted with —OH, —SH, —OR, —SR or —COOR where R is alkyl or alkenyl of up to 6 carbon atoms, thiazole, thiophene or $R_1$ and $R_2$ together with the basic nitrogen atom are piperidine or piperazine and $R_3$, $R_4$, $R_5$ and $R_6$ are hydrogen alkyl of up to 6 carbon atoms, alkenyl of up to 6 carbon atoms, phenyl, halophenyl, alkylphenyl having up to 3 carbon atoms in the alkyl group or either $R_3$ and $R_4$ or $R_5$ and $R_6$ together with the adjacent carbon atom of the thiazolidine ring from a cycloalkylene ring of 5 to 6 carbon atoms.

7. A process according to claim 6 wherein the compound has Formula III.

8. A process according to claim 7 wherein not over 2 of $R_3$, $R_4$, $R_5$ and $R_6$ are hydrogen.

9. A process according to claim 8 wherein the compound of formula III is 2,2,5,5-tetramethyl thiazolidine-4-carboxylic acid.

10. A process according to claim 8 wherein the compound of formula III is 2,2-pentamethylene-5,5-dimethyl-thiazolidine-4-carboxylic acid.

11. A process according to claim 7 wherein when $R_5$ and $R_6$ together with the adjacent carbon atom of the thiazolidine ring from a cycloalkylene ring the ring has 5 to 6 carbon atoms.

12. A process according to claim 1 consisting of carrying out the formylation with an alkali formate or ammonium formate in an inert organic solvent having a solubility in water of not over 50 grams per 100 grams of water.

13. A process according to claim 1 wherein the inert organic solvent has a solubility in water of not over 10 grams per 100 grams of water.

14. The process of claim 1 wherein the salt is the salt of an acid at least as strong as phosphoric acid.

15. A process according to claim 14 wherein the salt is a salt of a hydrohalic acid.

16. A process according to claim 15 wherein the hydrohalic acid is hydrochloric acid.

17. A process according to claim 1 wherein the salt of the nitrogen compound is 2,2,5,5,-tetramethyl thiazolidine-4-carboxylic acid hydrochloride, there are used about equivalent amounts of the nitrogen and compound and formate and the solvent is an aliphatic hydrocarbon, an aromatic hydrocarbon, an aliphatic halohydrocarbon or an ether.

18. A process according to claim 1 wherein the amount of formate ranges from an amount equivalent to the nitrogen compound to an excess of 100% over that amount.

* * * * *